United States Patent [19]

Payne

[11] Patent Number: 5,422,928
[45] Date of Patent: Jun. 6, 1995

[54] APPARATUS FOR MOUNTING A BACKBOARD TO A GURNEY

[76] Inventor: Cham N. Payne, 2576 Dunn Ave., Memphis, Tenn. 38114

[21] Appl. No.: 293,175

[22] Filed: Aug. 19, 1994

[51] Int. Cl.6 .............................................. H05G 1/02
[52] U.S. Cl. .................................... 378/177; 378/208; 378/209
[58] Field of Search ............... 378/167, 177, 178, 179, 378/180, 181, 182, 208, 209; 5/601, 625

[56] References Cited

U.S. PATENT DOCUMENTS

| | | | |
|---|---|---|---|
| 4,067,565 | 1/1978 | Daniels | 269/328 |
| 4,193,148 | 3/1980 | Rush | 5/86 |
| 4,651,564 | 3/1987 | Hayton et al. | 5/60 |
| 4,893,323 | 1/1990 | Cook, III | 378/177 X |
| 4,947,418 | 8/1990 | Barr et al. | 378/177 |
| 5,138,646 | 8/1992 | Hubert et al. | 378/177 |
| 5,155,758 | 10/1992 | Vogl | 378/209 |
| 5,166,968 | 11/1992 | Morse | 378/177 |
| 5,243,639 | 9/1993 | Johnson | 378/180 |
| 5,255,303 | 10/1993 | DiMaio et al. | 378/177 |

Primary Examiner—David P. Porta
Attorney, Agent, or Firm—Walker, McKenzie & Walker

[57] ABSTRACT

An apparatus for use in combination with a gurney, an X-ray transparent backboard and an X-ray cassette for allowing the backboard to be coupled to the gurney and for allowing the X-ray cassette to be coupled to the backboard. The apparatus includes an elongated body having a first end, a second end, a lower side for engaging the gurney, and an upper side for supporting the backboard; and slide structure coupled to the body for holding the X-ray cassette and for allowing the X-ray cassette to be moved back and forth along the body so that X-rays can be taken of a patient supported by the backboard without requiring the patient to be moved relative to the backboard.

17 Claims, 2 Drawing Sheets

APPARATUS FOR MOUNTING A BACKBOARD TO A GURNEY

BACKGROUND OF THE INVENTION

1. Field of the Invention

The present invention relates to means for use in hospital emergency rooms and the like for allowing a backboard with a patient supported thereof to be positioned on a gurney and for allowing typical X-ray cassettes to be accurately positioned and adjusted beneath the patient without requiring the patent to be removed from the backboard.

2. Information Disclosure Statement

In a medical emergency, a patient who may have a spinal injury or the like is normally secured to a backboard to insure that the patient's spine is maintained substantially immobile as the patient is transported to a hospital, etc. Once at the hospital, it is normally desired to take a plurality of X-rays of the patient to verify if any damage has occurred to the patient's spine, etc. Currently, such a patient is either transferred from the backboard to an X-ray table or other support for allowing X-rays to be taken using an X-ray machine, or raised somewhat off the backboard to allow an X-ray cassette to be placed beneath the patient so that X-rays can then be taken while the patient remains on the backboard.

A preliminary patentability search conducted in class 378, subclass 177, and class 5, subclass 601 produced the following patents which appear to be relevant to the present invention:

Daniels, U.S. Pat. No. 4,067,565, issued Jan. 10, 1978, discloses a premature infant immobilizer and holding assembly for the nursery and radiological exposure.

Russ, U.S. Pat. No. 4,193,148, issued Mar. 18, 1980, discloses a transparent radiation penetrable stretcher panel.

Hayton et al., U.S. Pat. No. 4,651,364, issued Mar. 24, 1987, discloses an X-ray cassette holder for a trauma stretcher.

Barr et al, U.S. Pat. No. 4,947,418, issued Aug. 7, 1990, discloses an emergency trauma board having dual, spaced apart main frames.

Vogl, U.S. Pat. No. 5,155,758, issued Oct. 13, 1992, discloses a portable device for facilitating the performance of radiographic procedures.

Nothing in the known prior art discloses or suggests the present invention. More specifically, nothing in the known prior art discloses or suggests an apparatus for use in combination with a gurney, an X-ray transparent backboard and an X-ray cassette for allowing the backboard to be coupled to the gurney and for allowing the X-ray cassette to be coupled to the backboard, and including an elongated body having a first end, a second end, a lower side for engaging the gurney, and an upper side for supporting the backboard; and slide means coupled to the body for holding the X-ray cassette and for allowing the X-ray cassette to be moved back and forth along the body so that X-rays can be taken of a patient supported by the backboard without requiring the patient to be moved relative to the backboard.

SUMMARY OF THE INVENTION

The present invention provides a device for assisting medical personnel in more efficiently and safely dealing with a patient who is confined to a backboard and required to submit to X-Rays. A basic concept of the present invention is to provide an apparatus including an elongated body having a lower side for engaging a gurney and an upper side for supporting an X-ray transparent backboard, and including slide means coupled to the body for holding an X-ray cassette and for allowing the X-ray cassette to be moved back and forth along the body so that X-rays can be taken of a patient supported by the backboard without requiring the patient to be moved relative to the backboard.

The apparatus of the present invention is for use in combination with a gurney, an X-ray transparent backboard, and an X-ray cassette for allowing the backboard to be coupled to the gurney and for allowing the X-ray cassette to be coupled to the backboard, and includes, in general, an elongated body having a first end, a second end, a lower side for engaging the gurney, and an upper side for supporting the backboard; and slide means coupled to the body for holding the X-ray cassette and for allowing the X-ray cassette to be moved back and forth along the body so that X-rays can be taken of a patient supported by the backboard without requiring the patient to be moved relative to the backboard.

DESCRIPTION OF THE PREFERRED EMBODIMENT

Figure 1:
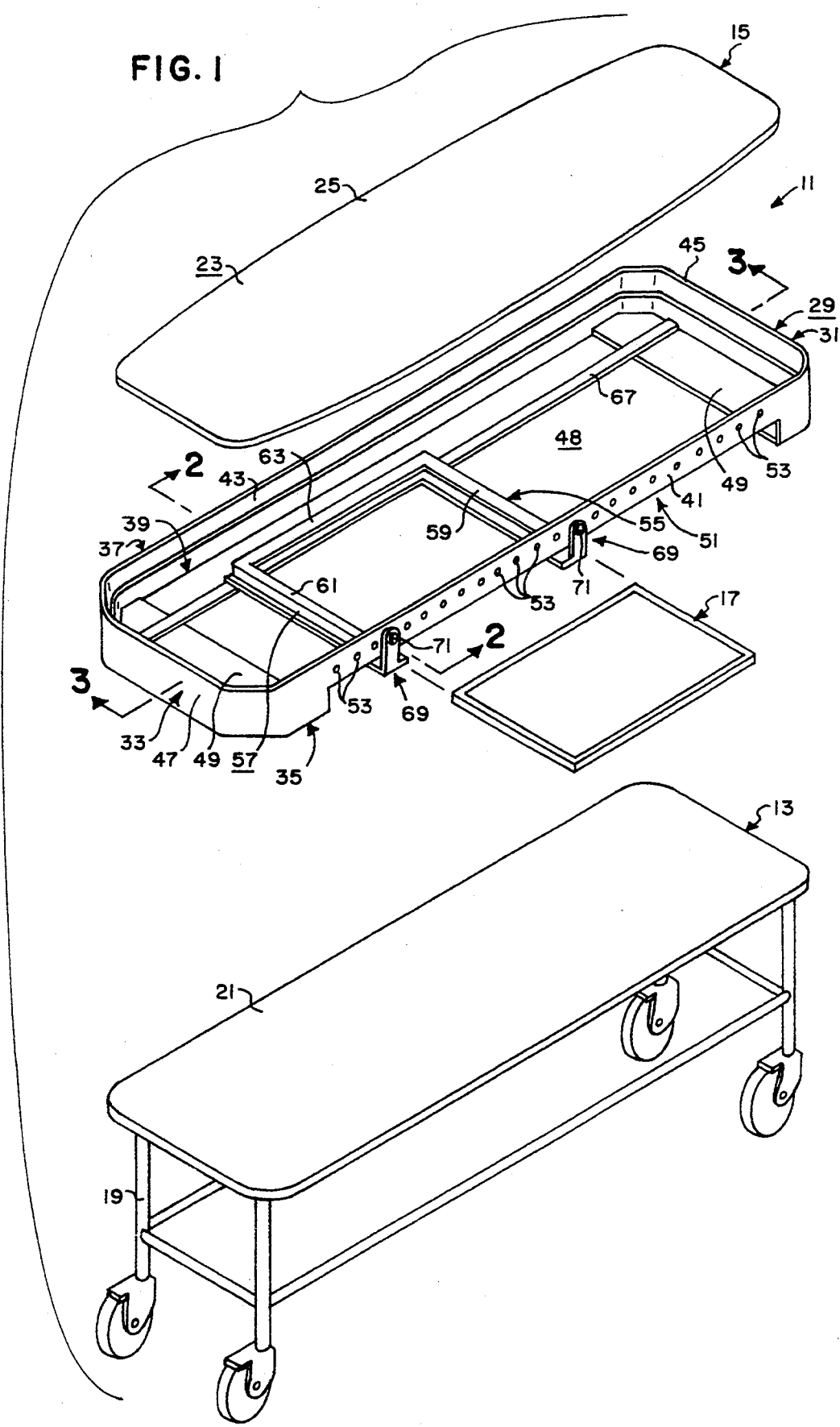
FIG. 1 is an exploded perspective view of the apparatus of the present invention, shown in combination with a gurney, a backboard, and an X-ray cassette.

A preferred embodiment of the apparatus of the present invention is shown in FIGS. 1-5, and identified by the numeral 11. The apparatus 11 is for use in combination with a gurney 13, an X-ray transparent backboard 15, and one or more X-ray cassettes 17 for allowing the backboard 15 to be coupled to the gurney 13 and for allowing the X-ray cassette 17 to be coupled to the backboard 15.

The gurney 13 may be of any typical construction well know to those skilled in the art. Thus, the gurney 13 may include a wheeled frame 19, and a support member 21 such as a mattress or the like on top of the frame 19 for supporting a patient and for allowing the patient to be easily moved around while lying on the support member 21 etc.

The backboard 15 may consist of a rigid body or plate-like member 23 having a substantially flat upper surface 25 for receiving a patient and a lower surface 27. The plate-like member 23 may have means such as slots or the like for allowing the backboard 15 to be easily picked-up and carried by emergency rescue workers or hospital workers, etc. Belts or the like might be provided for allowing the patient to be secured to the upper surface 25 of the plate-like member 23. It is critical that at least the plate-like member 23 of the backboard 15 be constructed of a durable, strong, rigid, X-ray transparent or penetrable, radiotransparent material such as, for example, molded polyethylene or the like which will safely support the patient while allowing X-rays of the patient to be taken therethrough with no interference. Any belt or the like used to secure the patient to the plate-like member 23 should also be constructed of X-ray transparent material. The size and shape of the backboard 15 may vary depending on the size and shape of the intended patients. Thus, for example, the backboard 15 may be provided in a small size for children, a large size for average adult patients, etc., as will now be apparent to those skilled in the art.

The apparatus 11 includes an elongated body 29 having a first end 31, a second end 33, a lower side 35 for engaging the gurney 13, and an upper side 37 for supporting the backboard 15. The upper side 37 of the body 29 preferably has a recess 39 therein for receiving the backboard 15. The body 29 preferably incudes a first side rail 41, a second side rail 43, a first end rail 45, and a second end rail 47 with the rails 41, 43, 45, 47 coacting to form the boundary of the recess 39. The body 29 preferably has a cavity 48 extending between the first and second ends 31, 33 thereof. More specifically, the cavity 48 preferably coacts with the recess 39 so that the body 29 is substantially open between the lower and upper sides 35, 37, between the first and second side rails 41, 43, and between the first and second end rails 45, 47, except for a ledge 49 adjacent each end rail 45, 47 as clearly shown in the drawings. The upper edge of each rail 41, 43, 45, 47 preferably has a off-set portion 50 for receiving the respective edge of the body 25 of the backboard 15. The first side rail 41 preferably has a slot 51 therein that extends substantially between the first and second end rails 45, 47 and that communicates with the recess 39 and the open lower side 35 of the body 29. The body 29 preferably has a plurality of spaced cavities or apertures 53 in the first side rail 41 between the first and second ends thereof as clearly shown in FIG. 1.

Figure 5:
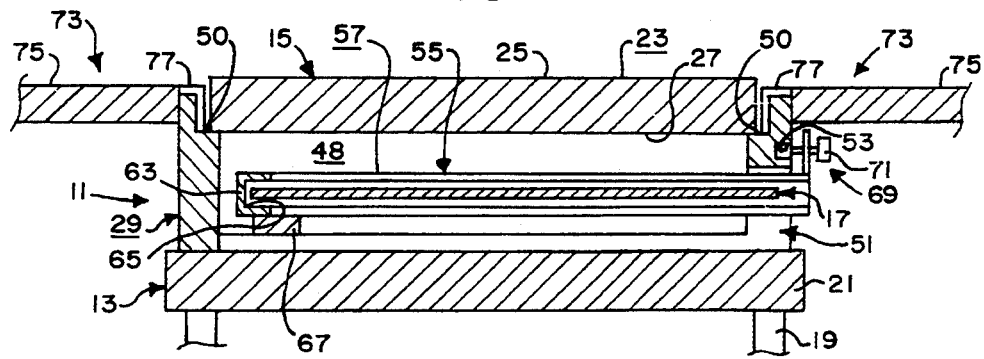
FIG. 5 is a sectional view substantially similar to FIG. 2 but showing the apparatus in combination with a gurney, a backboard and an X-ray cassette and with a pair of extension means shown attached to the body thereof.

The apparatus 11 includes slide means 55 coupled to the body 29 for holding the X-ray cassette 17 and for allowing the X-ray cassette 17 to be moved back and forth along the body 29 so that X-rays can be taken of a patient supported by the backboard 15 without requiring the patient to be moved relative to the backboard 15. The slide means 55 preferably includes a rigid frame member 57 slidably mounted within the cavity 48 of the body 29. The frame member 57 preferably includes a first side member 59, a second side member 61, and a end member 63 extending between the distal ends of the side members 59, 61, leaving one end of the frame member 57 open as shown in FIG. 5. Each member 59, 61, 63 preferably has a groove 65 therein for receiving a portion of the edge of the X-ray cassette 17 (see, for example, FIGS. 3 and 5) so that the X-ray cassette 17 can be easily inserted into the frame member 57 from the open end of the frame member 57. The slide means 55 may include lock means (not shown) for locking the X-ray cassette 17 to the frame member 57 when the X-ray cassette 17 is inserted thereinto. The lock means may consist of a simple spring-loaded mechanism for pressing against the X-ray cassette 17 as the X-ray cassette 17 is inserted into the frame member 57 and for holding the X-ray cassette 17 in the frame member 57 as an X-rays is taken while allowing the X-ray cassette 17 to be easily manually removed from the frame member 57.

Figure 2:
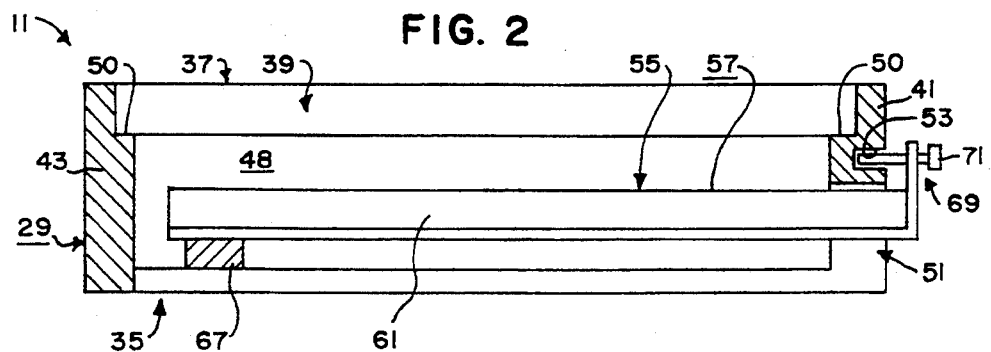
FIG. 2 is an enlarged sectional view of the apparatus of the present invention substantially as taken on line 2—2 of FIG. 1.
Figure 3:
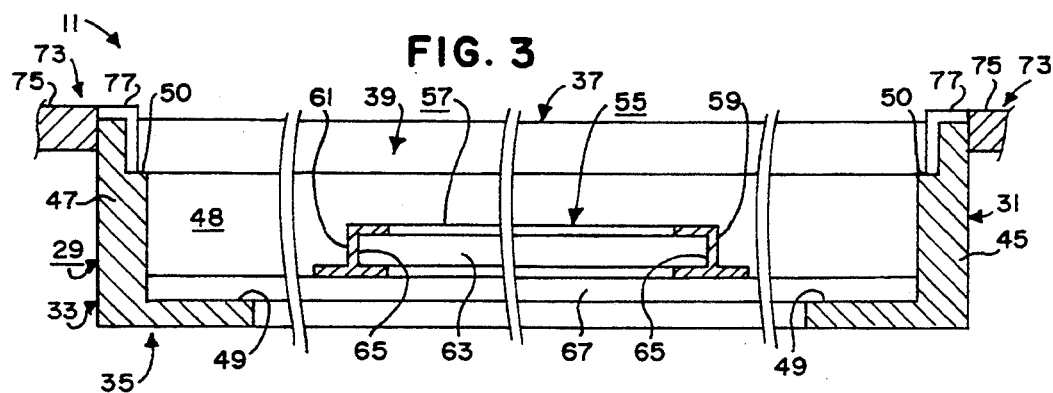
FIG. 3 is an enlarged sectional view of the apparatus of the present invention substantially as taken on line 3—3 of FIG. 1 with portions thereof broken away for clarity and with a pair extension means shown attached to the body thereof.
Figure 4:
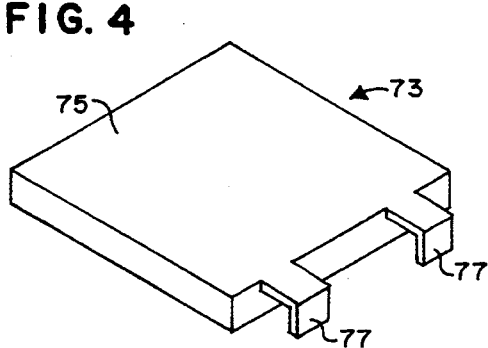
FIG. 4 is a perspective view of one preferred embodiment of an extension means of the apparatus of the present invention.

The apparatus 11 may include a support bar 67 extending between the first and second end rails 45, 47 of the body 29 across the open lower side 35 of the body 29 for supporting a distal portion of the slide means 55 as shown in FIGS. 1, 2 and 5. The support bar 67 may be constructed separate from the body 29 or may be constructed as a integral unit with the body 29.

The apparatus 11 preferably includes lock means 69 for locking the frame member 57 of the slide means 55 in any one of a plurality of positions between the first and second ends 31, 33 of the body 29. The lock means 69 may include one or more pin members 71 for extending through a portion of the frame member 57 and into one of the apertures 53 in the first side rail 41 of the body 29 to lock the frame member 57 in any one of a plurality of positions between the first and second ends 31.33 of the body 29. A pin member 71 may be slidably attached to the proximal end of each side member 59, 61 of the frame member 57 as clearly shown in FIG. 1. Each pin member 71 may be urged toward a locked position within one of the apertures 53 by a spring or the like (not shown) so that both pin members 71 can be manually pulled out to an unlocked position and the frame member 57 manually slides back and forth within the cavity 48 of the body 29 until it is positioned beneath the portion of a patient's body to be X-rayed. The pin members 71 can then be released so that they will extend into the appropriate apertures 53 to thereby lock the frame member 57 in place as will now be apparent to those skilled in the art. It will be understood that if the pin members 71 are not aligned with apertures 53 when released, it will be necessary to slightly move the frame member 57 back and forth until the pin members 71 align with the closest apertures 53.

The apparatus 11 preferably includes one or more extension means 73 for attachment to the body 29 and for providing an extension of the backboard 15. Each extension means 73 preferably includes a support surface 75 for supporting a portion of a patient's body. Each extension means 73 includes hook means 77 for hooking over a portion of the upper side 37 of the body 29 to secure the extension means 73 to the body 29 when the backboard 15 is supported on the upper side 37 of the body 29. The hook means 77 are especially designed so that each extension means 73 can be hooked onto and secured to a selected one of the rails 41, 43, 45, 47 of the body 29 to thereby allow the upper surface 25 of the plate-like member 23 of the backboard 15 to be effectively extended on the right side, left side, head and/or foot thereof. Such extensions can be critical when, for example, it is desired to extend one of the patient's arm while an X-ray is being taken, etc., as will now be apparent to those skilled in the art. The size and shape of the extension means 73 can vary depending on intended use, etc.

The apparatus 11 may be constructed in various manners, out of various materials, and in various sizes as will now be apparent to those skilled in the art. Preferably, the body 29, frame member 57, support bar 67, pin members 71, and extension means 73 are molded or otherwise constructed from a durable, strong, rigid, X-ray transparent or penetrable, radiotransparent material such as, for example, molded polyethylene or the like which will safely support the patient and backboard 15 while allowing X-rays of the patient to be taken therethrough with no interference.

To use the apparatus 11 of the present invention, when a patient is brought into an emergency room or the like on a backboard 15 and it is desired to take X-rays of the patient's spine, etc., before moving the patient from the backboard 15, the backboard 15, when the patient strapped or otherwise secured thereto, is merely placed into the recess 39 in the upper side 37 of the body 29. If desired, the patient and/or backboard 15 can be additionally secured to the body 29 by straps or the like, not shown. The combination of the patent, the backboard 15 and the body 29 can be supported on the support member 21 of the gurney 13 for transport to an X-ray room or the like. If desired, the patient and/or backboard 15 and/or body 29 can be additionally secured to the gurney 13 by straps or the like, not shown. The combination of the patent, the backboard 15 and the body 29 can be safely transferred from the gurney 13 to an X-ray table or the like. One or more X-rays can be taken by merely inserting a X-ray cassette 17 into the frame member 57 and moving the frame member 57 back and forth between the ends 31, 33 of the body 29 to properly and accurately position the X-ray cassette 17 beneath the portion of the patient's body to be X-rayed, etc., as will now be apparent to those skilled in the art.

Although the present invention has been described and illustrated with respect to a preferred embodiment and preferred uses therefor, it is not to be so limited since modifications and changes can be made therein which are within the full intended scope of the invention.

I claim:

1. The combination with a gurney, an X-ray transparent backboard and an X-ray cassette, of an apparatus for allowing the backboard to be coupled to the gurney and for allowing the X-ray cassette to be coupled to the backboard; said apparatus comprising:
   (a) an elongated body having a first end, a second end, a lower side for engaging the gurney, and an upper side for supporting the backboard; and
   (b) slide means coupled to said body for holding the X-ray cassette and for allowing the X-ray cassette to be moved back and forth along said body so that X-rays can be taken of a patient supported by the backboard without requiring the patient to be moved relative to the backboard.

2. The combination of claim 1 in which said upper side of said body of said apparatus has a recess for receiving the backboard.

3. The combination of claim 1 in which said apparatus includes extension means for attachment to said body and for providing an extension of the backboard.

4. The combination of claim 3 in which said extension means of said apparatus includes a support surface for supporting a portion of a patient's body.

5. The combination of claim 4 in which said extension means includes hook means for hooking over a portion of said upper side of said body of said apparatus to secure said extension means to said body when the backboard is supported on said upper side of said body of said apparatus.

6. The combination of claim 5 in which said body incudes a first side rail, a second side rail, a first end rail, and a second end rail; and in which said extension means can be hooked onto a selected one of said rails of said body.

7. The combination of claim 6 in which apparatus includes a plurality of said extension means.

8. The combination of claim 1 in which said body has a cavity extending between said first and second ends thereof; and in which said slide means includes a frame member slidably mounted within said cavity of said body.

9. The combination of claim 8 in which said apparatus includes lock means for locking said frame member in any one of a plurality of positions between said first and second ends of said body.

10. The combination of claim 9 in which said body has a plurality of apertures therein between said first and second ends thereof; and in which said lock means includes an pin member for extending through a portion of said frame member and into one of said apertures in said body to lock said frame member in any one of a plurality of positions between said first and second ends of said body.

11. The combination of claim 10 in which said lock means includes a pair of said pin members.

12. The combination of claim 6 in which lower side of said body is open between said first and second side rails; and in which is included a support bar extending between said first and second end rails of said body across the open lower side of said body for supporting a portion of said slide means.

13. The combination with a gurney, an X-ray transparent backboard and an X-ray cassette, of an apparatus for allowing the backboard to be coupled to the gurney and for allowing the X-ray cassette to be coupled to the backboard; said apparatus comprising:
   (a) an elongated body having a first end, a second end, a lower side for engaging the gurney, and an upper side for supporting the backboard; said body including a first side rail, a second side rail, a first end rail, and a second end rail; said body having a cavity extending between said first and second ends thereof;
   (b) slide means coupled to said body for holding the X-ray cassette and for allowing the X-ray cassette to be moved back and forth along said body so that X-rays can be taken of a patient supported by the backboard without requiring the patient to be moved relative to the backboard; said slide means including a frame member slidably mounted within said cavity of said body;
   (c) extension means for attachment to said body and for providing an extension of the backboard; said extension means including a support surface for supporting a portion of a patient's body; said extension means including hook means for hooking onto a selected one of said rails of said body to secure said extension means to said body when the backboard is supported on said upper side of said body of said apparatus; and
   (d) lock means for locking said frame member in any one of a plurality of positions between said first and second ends of said body.

14. The combination of claim 13 in which said upper side of said body of said apparatus has a recess for receiving the backboard.

15. The combination of claim 13 in which apparatus includes a plurality of said extension means.

16. The combination of claim 13 in which said body has a plurality of apertures therein between said first and second ends thereof; and in which said lock means includes a pair of pin members for extending through a portion of said frame member and into a respective one of said apertures in said body to lock said frame member in any one of a plurality of positions between said first and second ends of said body.

17. The combination of claim 13 in which lower side of said body is open between said first and second side rails; and in which is included a support bar extending between said first and second end rails of said body across the open lower side of said body for supporting a portion of said slide means.

* * * * *